(12) United States Patent
Grünwald

(10) Patent No.: US 11,596,376 B2
(45) Date of Patent: Mar. 7, 2023

(54) PROVIDING CORRECTED X-RAY IMAGES

(71) Applicant: Oxana Grünwald, Forchheim (DE)

(72) Inventor: Oxana Grünwald, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 1071 days.

(21) Appl. No.: 15/786,355

(22) Filed: Oct. 17, 2017

(65) Prior Publication Data

US 2018/0103922 A1   Apr. 19, 2018

(51) Int. Cl.
*A61B 6/00* (2006.01)
*G06T 11/00* (2006.01)
(Continued)

(52) U.S. Cl.
CPC ............ *A61B 6/5258* (2013.01); *A61B 6/481* (2013.01); *A61B 6/505* (2013.01); *A61B 6/5241* (2013.01); *G06T 5/002* (2013.01); *G06T 5/50* (2013.01); *G06T 7/0014* (2013.01); *G06T 7/136* (2017.01); *G06T 11/005* (2013.01); *G06T 11/008* (2013.01); *A61B 6/03* (2013.01); *A61B 6/488* (2013.01); *A61B 6/5235* (2013.01); *G06T 2207/10116* (2013.01);
(Continued)

(58) Field of Classification Search
CPC ....... A61B 6/5258; A61B 6/481; A61B 6/505; A61B 6/5241; G06T 7/136; G06T 7/0014; G06T 5/50; G06T 11/005; G06T 11/008
See application file for complete search history.

(56) References Cited

U.S. PATENT DOCUMENTS

2002/0165686 A1   11/2002   Kropfeld et al.
2006/0120507 A1    6/2006   Brunner et al.
(Continued)

FOREIGN PATENT DOCUMENTS

DE    10112792 A1     10/2002
DE    102004057308 A1  7/2006
DE    102013222674 B3  10/2014

OTHER PUBLICATIONS

German Office Action for German Application No. 102016220347.9, dated Jun. 20, 2017.
(Continued)

*Primary Examiner* — Ashley K Buran
*Assistant Examiner* — Marjan Saboktakin
(74) *Attorney, Agent, or Firm* — Lempia Summerfield Katz LLC

(57) ABSTRACT

A method for providing corrected x-ray images of a recording object and a correspondingly configured x-ray system are provided. In the method, a first x-ray image recorded prior to introducing a contrast agent and a second x-ray image of the recording object recorded after introducing the contrast agent are provided. A ring correction for eliminating ring artifacts is applied to the first x-ray image and the second x-ray image in each case. In order to provide corrected x-ray images with an improved image quality, provision is made with the ring correction of the first x-ray image for a ring image, which contains artifact data extracted from the first x-ray image, to be obtained and stored and for the ring correction of the second x-ray image for the ring image obtained with the ring correction of the first x-ray image to be used.

17 Claims, 2 Drawing Sheets

(51) Int. Cl.
  *G06T 5/00*   (2006.01)
  *G06T 7/136*  (2017.01)
  *G06T 5/50*   (2006.01)
  *G06T 7/00*   (2017.01)
  *A61B 6/03*   (2006.01)

(52) U.S. Cl.
  CPC .............. *G06T 2207/20221* (2013.01); *G06T 2207/20224* (2013.01); *G06T 2207/30008* (2013.01); *G06T 2207/30016* (2013.01)

(56) References Cited

U.S. PATENT DOCUMENTS

| | | | |
|---|---|---|---|
| 2010/0208969 A1* | 8/2010 | Ohishi | G06T 5/003 382/132 |
| 2011/0038458 A1 | 2/2011 | Spahn | |
| 2015/0126862 A1 | 5/2015 | Pfister | |
| 2015/0313565 A1* | 11/2015 | Matsuda | A61B 6/032 378/19 |
| 2015/0325011 A1* | 11/2015 | Ashida | A61B 6/504 382/131 |
| 2018/0350113 A1* | 12/2018 | Goto | G06T 11/006 |

OTHER PUBLICATIONS

Prell, Daniel, Yiannis Kyriakou, and Willi A. Kalender. "Comparison of ring artifact correction methods for flat-detector CT." Physics in medicine and biology 54.12 (2009): 3881.

Zellerhoff, M., et al. "Low contrast 3D reconstruction from C-arm data" Proc. of SPIE vol. vol. 5745. 2005.

* cited by examiner

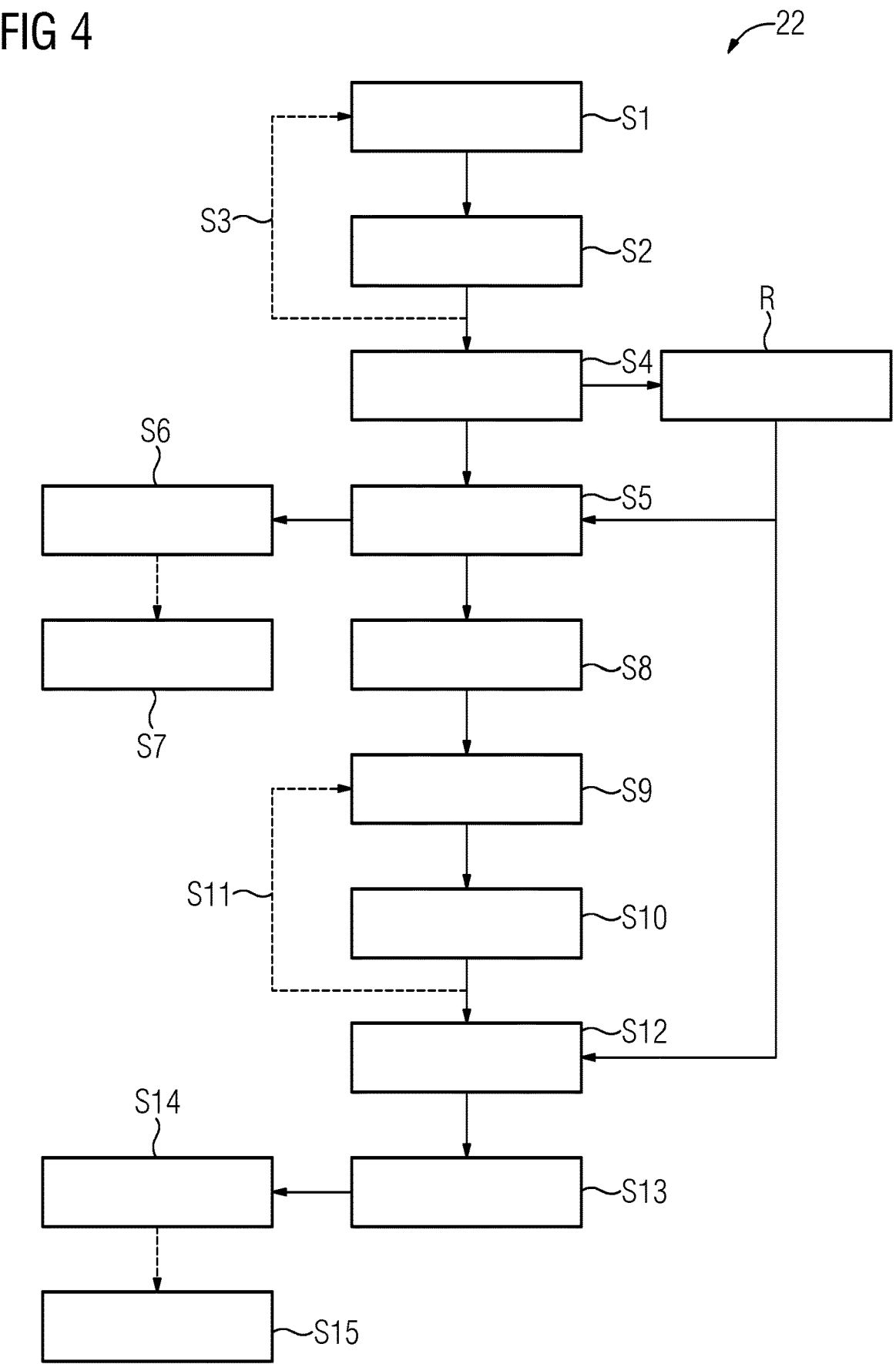

PROVIDING CORRECTED X-RAY IMAGES

This application claims the benefit of DE 10 2016 220 347.9, filed on Oct. 18, 2016, which is hereby incorporated by reference in its entirety.

BACKGROUND

The present embodiments relate to providing corrected x-ray images.

C-arm x-ray systems as interventional systems in radiology are known from the prior art. A two-dimensional live or real-time imaging during a catheter intervention, for example, represents one original use of these x-ray systems. Ongoing technical developments make it possible to also acquire CT-like images using these x-ray systems. Since then, a process and a level of safety for different treatments have been improved by an imaging of this type.

It is known from medical practice, for example, to create a first x-ray image of a recording object (e.g., of a patient) using a C-arm x-ray system, then to introduce a contrast agent into the patient, and finally, while the contrast agent is inside the patient, to record a further x-ray image. By comparing these two x-ray images, a significant amount of medical and diagnostically valuable information and knowledge may be obtained. However, with conventional x-ray systems, it is disadvantageous that ring artifacts are produced in the x-ray images or x-ray recordings by a detector and an anti-scatter grid provided to reduce scattered radiation upstream of the detector. These ring artifacts typically have a structure made up of rings or circles (e.g., concentric rings or circles) and reduce a quality and usability of the x-ray images, since the ring artifacts do not contain any information relating to the recorded or x-rayed recording object.

Ring correction methods for removing such ring artifacts from the recorded x-ray images or the corresponding data records are known from the prior art. However, previously known and also used ring correction methods or procedures produce other artifacts or image disturbances in the x-ray images. Vascular edge artifacts appear, for example, when known ring correction methods are applied to x-ray images with a high contrast. These vascular edge artifacts are typically found in x-ray images recorded with the use of a contrast agent and may be seen in close proximity to vessels marked particularly clearly by the contrast agent (e.g., blood vessels).

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method for providing corrected x-ray images and a corresponding x-ray system that supplies corrected x-ray images with improved image quality are provided.

In one embodiment, a method for providing corrected x-ray images of a recording object provides that a first x-ray image recorded prior to introducing a contrast agent into the recording object and a second x-ray image of the recording object recorded after introducing the contrast agent are provided. The second x-ray image may be or may have been recorded, for example, while the contrast agent is/was still at least partially inside the recording object. In such cases, the recording object may be any object (e.g., a patient) or also a corresponding subregion. The method of one or more of the present embodiments provides that a ring correction for eliminating ring artifacts is applied to the first x-ray image and the second x-ray image in each case. A ring correction may be a measure or methodology that serves, solely by devices or facilities used respectively when recording the first x-ray image and the second x-ray image, to eliminate, reduce, and/or filter out from the respective x-ray image or a corresponding data record or image data record, specific artifacts or image disturbances with an at least approximately ring-shaped or circular structure. To provide corrected x-ray images with improved image quality, with the ring correction of the first x-ray image, a ring image that contains artifact data extracted from the first x-ray image is obtained and stored according to one or more of the present embodiments. For ring correction of the second x-ray image, this ring image obtained with the ring correction of the first x-ray image is then used.

The first x-ray image is also referred to as the mask image or mask, while the second x-ray image is also referred to as the fill image or filling. The first x-ray image is recorded, for example, without contrast agent (e.g., without a contrast agent being present in the recording object or having been introduced into the recording object immediately beforehand). The first x-ray image, as a neutral x-ray image (e.g., not influenced by additional or external influences or measures), may thus represent a base or reference. Since no contrast agent is used to record or obtain or generate the first x-ray image, there are advantageously no influences, image artifacts, or image errors caused directly or indirectly by a contrast agent or an increased contrast. Through the use of the ring image obtained from the first x-ray image for ring correction of the second x-ray image, advantageously no additional artifacts, image errors, or image disturbances (e.g., no vascular edge artifacts) are also produced in this second x-ray image despite a contrast increased by the contrast agent. The ring correction of the second x-ray image may advantageously be carried out in this way with a considerably reduced computing or data processing outlay and thus also significantly more quickly compared with conventional methods. Compared with known methods, the significantly improved image quality that may be achieved with the method according to one or more of the present embodiments after applying the ring correction is of increasing importance with increased resolution and sharpness and/or feature differentiation from increasingly improved and further-developed x-ray devices or x-ray systems. Using the improved image quality (e.g., the corrected second x-ray image), it is immediately considerably easier for a user (e.g., a treating physician) to view, interpret, and understand the corrected x-ray images in terms of medical considerations. This advantageously also results in an increasing or increased level of trust among respective customers or users, but also among respective patients, in an x-ray system employed to carry out the method. Overall, a ring correction may advantageously also be applied successfully by the present embodiments with very high-contrast x-ray images, without disadvantageous effects occurring in the process. For the present embodiments, the fact that with typical x-ray devices or x-ray systems the ring artifacts produced by the detector and the anti-scatter grid do not change or, at least with respect to an influence on an ultimate image quality, only change to a negligible or insignificant degree over relatively short time scales (e.g., the order of magnitude of a few seconds to up to a few minutes) is exploited. This provides that the rings or ring artifacts to be corrected in the mask image and in the filling or fill image are therefore the same with sufficient accuracy.

The provision of the first x-ray image and/or the second x-ray image may include recording with a corresponding x-ray device or, for example, may also signify a transfer or call-up of the first x-ray image and/or the second x-ray image or a corresponding data record representing the first x-ray image and/or the second x-ray image from a storage facility (e.g., an electronic storage facility). The ring corrections may be performed or take place (e.g., also automatically), as part of an image processing or post-processing of the first x-ray image and the second x-ray image that is intended to be carried out routinely.

In a further embodiment of the method, the ring image obtained from the ring correction of the first x-ray image is subtracted from the second x-ray image for the purpose of ring correction of the second x-ray image. A subtraction of images in such cases signifies a, for example, pixel-by-pixel or pixel-based subtraction, for example, of respective brightness, intensity, tone, and/or color values of respective image data records, which represent the x-ray images, using corresponding suitable data processing methods. By subtracting the ring image from the second x-ray image, the ring correction of the second x-ray image may be carried out with as little computing outlay and time required as possible. The ring correction of the second x-ray image may thus be executed in a single processing or computing step, for example.

On account of the short processing time of the x-ray images or the x-ray image data that may be achieved with the present method, a quicker response by a treating physician or other qualified personnel may be permitted during an ongoing treatment, for example.

In a further embodiment of the method, in order to provide the first x-ray image and the second x-ray image, the first x-ray image and the second x-ray image may be recorded by an x-ray device in a temporal interval of at most 30 minutes (e.g., at most 15 minutes). Using a temporal interval that is limited in this way between the respective recording time points of the first x-ray image and the second x-ray image, it is possible to provide that an optimal image quality of the corrected x-ray images is achieved. This is based on it being possible to assume that the ring artifacts appearing in the first x-ray image and in the second x-ray image are then the same.

In a further embodiment of the method, multiple first x-ray images and second x-ray images that each represent a sectional image of the recording object to be recorded by an x-ray device in each case. The ring image of one of the multiple first x-ray images is then used in each case for the ring correction of a corresponding second x-ray image that represents the same sectional image. In other words, two runs or cycles of x-ray image recordings, in which in each case a plurality of single x-ray images are recorded or created, are therefore executed. Both before and also after introducing the contrast agent, a development or dynamic of the recording object may then be read out or identified or determined from the multiple single x-ray images by a respective image series. This provides that an optimal image quality of the corrected x-ray images is also achieved when different regions of the recording object are recorded within an image series or between the two image series. In one embodiment, a single ring image (e.g., a ring image of one of the multiple first x-ray images) may be used for the ring correction of all second x-ray images, particularly when a positioning or a movement of the recording object and/or the respectively used x-ray device or x-ray system is known and/or controlled sufficiently precisely. As a result, data processing effort may also be saved.

In a further embodiment of the method, the multiple first x-ray images may be combined to form a first three-dimensional x-ray image, and the multiple second x-ray images may be combined to form a second three-dimensional x-ray image. In other words, there is therefore provision for CT recordings or CT-type recordings to be produced. A reconstruction of the recording object is therefore carried out based on, for example, the respective x-ray image series. With such 3D recordings and/or when reviewing the 3D recordings in the form of a rapid sequence of single sectional images, the respective observer is not distracted, irritated, misled or misdirected by image artifacts.

In a further embodiment of the method, the recording object may include a biological tissue, and in order to obtain the ring image of the first x-ray image, a sequence of a first threshold value filter for segmenting bone tissue and metallic elements, a radial median filter, a second threshold value filter, and a median filter that functions in the circumferential direction of the ring artifacts may be applied hereto. As a result of these steps, a ring image that may contain only the pure ring artifacts of the respective image or sectional image or of the respective reconstructed slice is produced.

An x-ray system of one or more of the present embodiments has an x-ray device and an evaluation facility. The x-ray device includes a radiation source and a detector or image receiver, and the evaluation facility is connected hereto in order to receive x-ray images detected by the detector (e.g., via a corresponding data link). To supply or provide corrected x-ray images with improved image quality, the evaluation facility may include a processor facility (e.g., one or more processors) and a storage medium with a program code that is configured, when executed by the processor facility for providing corrected x-ray images, to apply in each case a ring correction for eliminating ring artifacts to a first x-ray image and a second x-ray image received by the evaluation facility. The program code is also configured during the ring correction of the first x-ray image to obtain a ring image that contains artifact data extracted from the first x-ray image, and to store the same in a storage facility. For ring correction of the second x-ray image, the execution of the program code causes the ring image obtained with the ring correction of the first x-ray image to be called up from the storage facility, and this ring image to be used for ring correction of the second x-ray image. The evaluation facility may, for example, be integrated into the x-ray device and/or connected with the x-ray device to form a compact unit. In one embodiment, the evaluation facility may represent a facility that is separate from the x-ray device and may be connected or coupled to the x-ray device solely via a corresponding data link. This data link may, for example, be a permanent or detachable line or a corresponding cable or may be realized entirely or partially also by a wireless data transmission technology. In one embodiment, the x-ray images detected by the detector in the form of corresponding data records may be transmitted onto a storage medium, and only then, this storage medium may be connected, coupled, or brought in contact with the evaluation facility in order then to transmit the x-ray images or x-ray image data records onto or into the evaluation facility from the storage medium.

The functional embodiments of the method and of the x-ray system described previously and below as well as in the claims and the corresponding advantages may be transferred in each case accordingly analogously alternately between the method and the x-ray system. This also applies to components, devices, and facilities that are or may be used to carry out the method.

BRIEF DESCRIPTION OF THE DRAWINGS

FIG. 4 shows a schematic flow diagram of an embodiment of the method.

DETAILED DESCRIPTION

Figure 1:
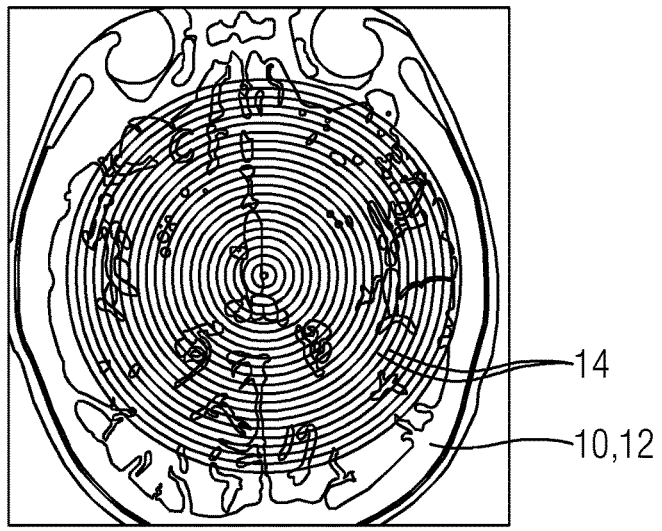
FIG. 1 shows a schematic diagram of an uncorrected x-ray image of a recording object with ring artifacts.

FIG. 1 shows a schematic diagram of an uncorrected second x-ray image 10 of a recording object 12. The second x-ray image 10 is recorded after contrast agent is injected into the recording object, while the contrast agent is at least partially still in the recording object. In the present case, the recording object is a human head and the second x-ray image 10 represents a sectional image. Since the second x-ray image 10 is displayed before applying a ring correction, ring artifacts 14 are contained and may be identified in the corresponding data that underlies the second x-ray image 10 shown.

Figure 2:
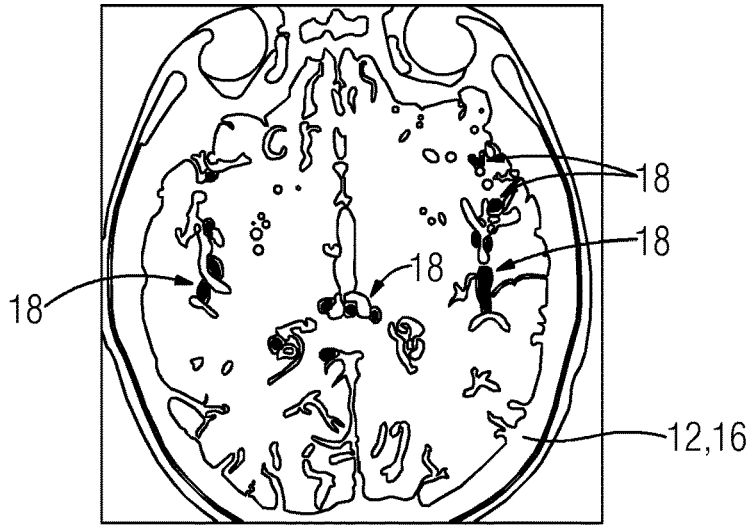
FIG. 2 shows a schematic diagram of the x-ray image from FIG. 1 after a ring correction with a conventional known method.

FIG. 2 shows a conventional corrected second x-ray image 16 that corresponds to the second x-ray image 10 from FIG. 1 after a ring correction carried out with a conventional known method. Additional artifacts or image errors in the form of vascular edge artifacts 18 are produced in the conventional corrected second ring image 16 as a result of this conventional ring correction. The conventional corrected second ring image 16 thus corresponds to the current prior art. With respect to the ring artifacts 14, although an improvement compared with the uncorrected second x-ray image 10 is illustrated, the additional introduction of unwanted vascular edge artifacts 18 disadvantageously influences the image quality of the conventional corrected second x-ray image 16. It is known that vascular edge artifacts 18, as a result of conventional ring correction methods, appear on highly contrasted vessels in x-ray images due to the contrast agent. This problem of vascular edge artifacts 18 caused by the fundamentally required, and with regards to image quality on the whole positive, ring correction has not yet been solved according to the current prior art and literature, and no method or solution for reducing or eliminating these specific artifacts or this specific type of artifact is currently known.

Figure 3:
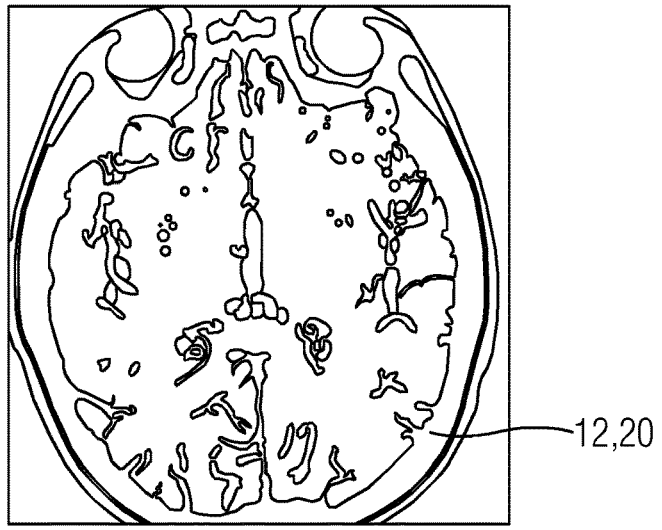
FIG. 3 shows a schematic diagram of the x-ray image from FIG. 1 after a ring correction carried out according to one or more of the present embodiments.

FIG. 3 shows a schematic view of a corrected second x-ray image 20, which corresponds to the second x-ray image 10 from FIG. 1 after a ring correction according to an embodiment of the present method. The corrected second x-ray image 20 has neither the ring artifacts 14 nor the vascular edge artifacts 18.

FIG. 4 shows a schematic diagram of a flow chart 22, based on which an exemplary embodiment of the present method for providing corrected x-ray images 20 of a recording object 12 is to be explained. In a first method act S1, a first x-ray image of the recording object 12 is recorded by an x-ray device. The x-ray device has at least one radiation source for x-ray radiation and a detector or image receiver. The x-ray device may be a C-arm CT x-ray device. In a method act S2, the first x-ray image is read out from the detector and provided to an evaluation facility. The evaluation facility may be, for example, a computing facility, a computer, or suchlike. The evaluation facility may also be or include a specialized electrical and/or electronic circuit or circuit arrangement. In an optional method act S3, the two previous method acts S1 and S2 may be run through repeatedly in order to obtain a series of multiple first x-ray images, based on which a reconstruction of a three-dimensional x-ray image of the recording object 12 is possible.

In a method act S4, a ring image calculation is carried out for the first x-ray image provided in method act S2, for one of the first x-ray images provided, or also for multiple or for all first x-ray images provided.

The method is described below in a representational and simplified manner based on a single first x-ray image, though the method may be used and may be carried out analogously for multiple first x-ray images or a series of first x-ray images.

A ring image R resulting from the ring image calculation is stored in a storage facility of the evaluation facility and is thus available for subsequent method acts. For the ring image calculation, a filter for segmenting bone tissue and metallic objects may be applied, for example, to the first x-ray image in a threshold value procedure so that a data or image value range is restricted to soft tissue. A radial median filter and then a second additional threshold value filter may then firstly be used for repeated or improved segmentation. After a subsequent application of a median filter that functions in the circumferential direction of the ring artifacts 14 and is circumferential (e.g., partial-circular), the result is the ring image R that thus contains only ring artifact data extracted from the first x-ray image.

Another method or another procedure may, however, also be used to calculate or obtain the ring image R, where additional and/or other filters and/or another application sequence of filters may, for example, be provided.

In method act S5, a final ring correction of the first x-ray image takes place, in which the ring image R is subtracted from the first x-ray image. Other correction measures, filters, and/or image processing and/or data processing steps may have already been applied to or may be applied to the first x-ray image prior to and/or after this subtraction. As a result of the ring correction of the first x-ray image, a corrected first x-ray image is produced, which is stored and provided in a method act S6 and is thus available for further method acts and/or other applications.

If multiple first x-ray images are recorded in the method act S3, the corrected first x-ray images may at this point be combined to form a 3D data record or 3D image.

On completion of the recording or obtaining of the first x-ray image or images, contrast agent is introduced or injected into the recording object in method act S8. In method act S9, a second x-ray image 10 of the same recording object is recorded while the contrast agent is at least partially still inside the recording object. This recording of the second x-ray image 10 may be carried out within 30 minutes (e.g., within 15 minutes) after the first x-ray image is recorded. In method act S10, the second x-ray image 10 or a corresponding data record that represents the second x-ray image 10 is also read out from the detector and is transferred or provided to the evaluation facility. In one embodiment, method acts S9 and S10 are run through in a method act S11 for recording and providing multiple second x-ray images 10 or a series of second x-ray images multiple times or repeatedly in the manner of a loop.

Once the second x-ray image 10 or all second x-ray images 10 have been recorded, the previously stored ring image R of the first x-ray image is called up in a method act S12 and is used for ring correction of the second x-ray image 10 in a method act S13. In the course of the ring correction or as the ring correction, the ring image R is subtracted from the second x-ray image. In one embodiment, further correction and/or data processing measures or suchlike may be applied to the second x-ray image 10 prior to and/or after this subtraction.

As a result of the method act S13, a corrected second x-ray image 20 is obtained, which contains or has neither ring artifacts 14 nor vascular edge artifacts 18. This corrected second x-ray image 20 is stored and provided in a method act S14 and is thus available for further method acts and/or for other applications or intended uses.

If multiple second x-ray images 10 or a series of second x-ray images 10 are recorded in method act S11, the corresponding corrected second x-ray images 20 may be combined in a method act S15 for reconstructing the recording object to form a 3D image.

The flow chart 22 only represents one example, and other measures may be performed or carried out prior to, between, or after the described method acts S1 to S15. Similarly, at least some of the described method acts S1 to S15 may also be carried out in a sequence other than that shown and described here. For example, multiple first and second x-ray images may each be held, for example, in a temporary store of the detector and then transmitted or provided in bundled form to the evaluation facility. The ring image calculation and storage as well as the ring correction and the combination of multiple first ring images may also be carried out, for example, after injecting the contrast agent or after recording the second ring image 10. Conversely, the first x-ray image is recorded prior to injecting the contrast agent, the second x-ray image 10 is recorded after injecting the contrast agent, and the ring image R is calculated, determined, or ascertained prior to the ring correction of the second x-ray image 10.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for providing corrected x-ray images of a recording object, the method comprising:
   providing a first x-ray image of the recording object, the first x-ray image being recorded prior to introducing a contrast agent into the recording object;
   providing a second x-ray image of the recording object recorded after introducing the contrast agent into the recording object;
   applying a ring correction for eliminating ring artifacts to the first x-ray image and the second x-ray image in each case, wherein a ring image that contains artifact data extracted from the first x-ray image is obtained from the ring correction of first ring artifacts present in the first x-ray image and stored; and
   using the ring image obtained with the ring correction of the first ring artifacts in the first x-ray image for the ring correction of second ring artifacts present in the second x-ray image.

2. The method of claim 1, wherein providing the second x-ray image of the recording object recorded after introducing the contrast agent comprises recording the second x-ray image while the contrast agent is at least partially inside the recording object.

3. The method of claim 1, wherein applying the ring correction to the second x-ray image comprises subtracting the ring image from the second x-ray image.

4. The method of claim 1, wherein providing the first x-ray image and the second x-ray image comprises recording the first x-ray image and the second x-ray image using an x-ray device in a temporal interval of at most 30 minutes.

5. The method of claim 4, wherein the first x-ray image and the second x-ray image are recorded using the x-ray device in a temporal interval of at most 15 minutes.

6. The method of claim 1, wherein multiple first x-ray images each representing a sectional image of the recording object, and multiple second x-ray images are recorded by an x-ray device in each case, and wherein in each case, the ring image of one of the multiple first x-ray images is used for the ring correction of a corresponding second x-ray image that represents the same sectional image in each case.

7. The method of claim 6, wherein the multiple first x-ray images are combined to form a first three-dimensional x-ray image, and the multiple second x-ray images are combined to form a second three-dimensional x-ray image.

8. The method of claim 1, wherein the recording object comprises a biological tissue, and
   wherein the method further comprises:
      obtaining the ring image of the first x-ray image, the obtaining of the ring image comprising:
         applying a first threshold value for segmenting bone tissue and metallic elements, a radial median filter, a second threshold value filter, and a median filter functioning in a circumferential direction of the ring artifacts to the first x-ray image.

9. An x-ray system comprising:
   an x-ray device; and
   an evaluation facility, wherein the x-ray device comprises a radiation source and a detector, and the evaluation facility for receiving x-ray images detected by the detector is connected to the detector, wherein the evaluation facility comprises a processor and a storage medium storing instructions executable by the processor to provide corrected x-ray images, the instructions comprising:
      applying, in each case, a ring correction for eliminating ring artifacts to a first x-ray image and a second x-ray image received by the evaluation facility, wherein the first x-ray image and the second x-ray image are recorded based on a same recording object;
      obtaining a ring image that contains ring artifact data extracted from the first x-ray image from the ring correction of first ring artifacts present in the first x-ray image and transmitting the ring image from the storage medium to an electronic storage facility; and
      for ring correction of second ring artifacts present in the second x-ray image, calling up from the electronic storage facility and using the ring image obtained with the ring correction of first ring artifacts present in the first x-ray image.

10. The x-ray system of claim 9, wherein the instructions further comprise recording the second x-ray image of the recording object after introducing a contrast agent.

11. The x-ray system of claim 10, wherein recording the second x-ray image of the recording object after introducing the contrast agent comprises recording the second x-ray image while the contrast agent is at least partially inside the recording object.

12. The x-ray system of claim 9, wherein applying the ring correction to the second x-ray image comprises subtracting the ring image from the second x-ray image.

13. The x-ray system of claim 9, wherein the instructions further comprise providing the first x-ray image and the second x-ray image, and
wherein providing the first x-ray image and the second x-ray image comprises recording the first x-ray image and the second x-ray image using an x-ray device in a temporal interval of at most 30 minutes.

14. The x-ray system of claim 13, wherein the first x-ray image and the second x-ray image are recorded using the x-ray device in a temporal interval of at most 15 minutes.

15. The x-ray system of claim 9, wherein multiple first x-ray images each representing a sectional image of the recording object, and multiple second x-ray images are recorded by an x-ray device in each case, and wherein in each case, the ring image of one of the multiple first x-ray images is used for the ring correction of a corresponding second x-ray image that represents the same sectional image in each case.

16. The x-ray system of claim 15, wherein the multiple first x-ray images are combined to form a first three-dimensional x-ray image, and the multiple second x-ray images are combined to form a second three-dimensional x-ray image.

17. The x-ray system of claim 9, wherein the recording object comprises a biological tissue, and
wherein the instructions further comprise:
obtaining the ring image of the first x-ray image, the obtaining of the ring image comprising:
applying a first threshold value for segmenting bone tissue and metallic elements, a radial median filter, a second threshold value filter, and a median filter functioning in a circumferential direction of the ring artifacts to the first x-ray image.

* * * * *

UNITED STATES PATENT AND TRADEMARK OFFICE
CERTIFICATE OF CORRECTION

PATENT NO. : 11,596,376 B2
APPLICATION NO. : 15/786355
DATED : March 7, 2023
INVENTOR(S) : Oxana Grünwald Page 1 of 1

It is certified that error appears in the above-identified patent and that said Letters Patent is hereby corrected as shown below:

On the Title Page

Add item (30), as follows:
(30) Foreign Application Priority Data:
October 18, 2016 (DE) ...................... 102016220347.9

Signed and Sealed this
Seventeenth Day of September, 2024

Katherine Kelly Vidal
*Director of the United States Patent and Trademark Office*